US00PP26759P2

(12) United States Plant Patent
van der Knaap

(10) Patent No.: US PP26,759 P2
(45) Date of Patent: May 24, 2016

(54) *SPATHIPHYLLUM* PLANT NAMED 'SPAMEI'

(50) Latin Name: ***Spathiphyllum* Schott**
Varietal Denomination: Spamei

(71) Applicant: Leonardus Johannes Maria van der Knaap, Naaldwijk (NL)

(72) Inventor: Leonardus Johannes Maria van der Knaap, Naaldwijk (NL)

(73) Assignee: Nubilus B.V., Naaldwijk (NL)

( * ) Notice: Subject to any disclaimer, the term of this patent is extended or adjusted under 35 U.S.C. 154(b) by 129 days.

(21) Appl. No.: 14/120,581

(22) Filed: Jun. 6, 2014

(51) Int. Cl.
*A01H 5/02* (2006.01)

(52) U.S. Cl.
USPC ..... Plt./364

(58) Field of Classification Search
USPC ..... Plt./364
See application file for complete search history.

*Primary Examiner* — Anne Grunberg
(74) *Attorney, Agent, or Firm* — C. A. Whealy

(57) ABSTRACT

A new and distinct cultivar of *Spathiphyllum* plant named 'Spamei', characterized by its upright, somewhat outwardly arching and uniform plant habit; freely clumping growth habit; bushy and dense plants; glossy dark green-colored leaves; freely flowering habit; large white-colored spathes that are positioned above and between the foliar plane on strong and erect scapes; flowers that do not produce pollen; and good inflorescence longevity.

2 Drawing Sheets

Botanical designation: *Spathiphyllum* Schott.
Cultivar denomination: 'SPAMEI'.

BACKGROUND OF THE INVENTION

The present invention relates to a new and distinct cultivar of *Spathiphyllum* plant, botanically known as *Spathiphyllum* Schott. and hereinafter referred to by the name 'Spamei'.

The new *Spathiphyllum* plant is a product of a controlled breeding program conducted by the Inventor in Naaldwijk, The Netherlands. The objective of the breeding program is to create new year-round flowering *Spathiphyllum* plants that have glossy dark green-colored leaves, large white-colored spathes and good postproduction longevity.

The new *Spathiphyllum* plant originated from a cross-pollination made by the Inventor in October, 2008 of a proprietary *Spathiphyllum* selection identified as code number 20051583-02, not patented, as the female, or seed, parent with a proprietary *Spathiphyllum* selection identified as code number 20071786-33, not patented, as the male, or pollen, parent. The new *Spathiphyllum* plant was discovered and selected by the Inventor as a single plant within the progeny of the stated cross-pollination in a controlled greenhouse environment in Naaldwijk, The Netherlands in January, 2010.

Asexual reproduction of the new *Spathiphyllum* plant by tissue culture in a controlled environment in Naaldwijk, The Netherlands since September, 2010 has shown that the unique features of this new *Spathiphyllum* plant are stable and reproduced true to type in successive generations of asexual reproduction.

SUMMARY OF THE INVENTION

Plants of the new *Spathiphyllum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Spamei'. These characteristics in combination distinguish 'Spamei' as a new and distinct *Spathiphyllum* plant:

1. Upright, somewhat outwardly arching and uniform plant habit.
2. Freely clumping growth habit; bushy and dense plants.
3. Glossy dark green-colored leaves.
4. Freely flowering habit.
5. Large white-colored spathes that are positioned above and between the foliar plane on strong and erect scapes.
6. Flowers that do not produce pollen.
7. Good inflorescence longevity.

Plants of the new *Spathiphyllum* differ from plants of the parent selections in the following characteristics:

1. Plants of the new *Spathiphyllum* are more upright than plants of the parent selections.
2. Plants of the new *Spathiphyllum* have darker green-colored leaves than plants of the parent selections.
3. Flowers of plants of the new *Spathiphyllum* do not produce pollen whereas flowers of plants of the parent selections produce pollen.

Plants of the new *Spathiphyllum* can also be compared to plants of *Spathiphyllum* spp. 'Sparanke', disclosed in U.S. Plant Pat. No. 21,294. In side-by-side comparisons conducted in Naaldwijk, The Netherlands, plants of the new *Spathiphyllum* differed from plants of 'Sparanke' in the following characteristics:

1. Plants of the new *Spathiphyllum* were more upright than plants of 'Sparanke'.
2. Plants of the new *Spathiphyllum* had darker green-colored leaves than plants of 'Sparanke'.

3. Flowers of plants of the new *Spathiphyllum* did not produce pollen whereas flowers of plants of 'Sparanke' produced pollen.

BRIEF DESCRIPTION OF THE PHOTOGRAPHS

The accompanying photographs illustrate the overall appearance of the new *Spathiphyllum* plant showing the colors as true as it is reasonably possible to obtain in colored reproductions of this type. Colors in the photographs may differ slightly from the color values cited in the detailed botanical description which accurately describe the colors of the new *Spathiphyllum* plant.

The photograph on the first sheet is a side perspective view of a typical plant of 'Spamei' grown in a container.

The photograph on the second sheet is a close-up view of a typical inflorescence of 'Spamei'.

DETAILED BOTANICAL DESCRIPTION

The aforementioned photographs and following observations and measurements describe plants grown during the spring in 17-cm containers in a glass-covered greenhouse in Naaldwijk, The Netherlands. Plants were grown under conditions and practices which approximate those generally used in commercial *Spathiphyllum* production. During the production of the plants, day temperatures ranged from about 19° C. to 24° C., night temperatures ranged from about 19° C. to 22° C. and light levels averaged 5 klux. Plants were 40 weeks old when the photographs and the detailed description were taken. In the following description, color references are made to The Royal Horticultural Society Colour Chart, 2007 Edition, except where general terms of ordinary dictionary significance are used.

Botanical classification: *Spathiphyllum* Schott. 'Spamei'.

Parentage:

*Female, or seed, parent.*—Proprietary selection of *Spathiphyllum* Schott. identified as code number 20051583-02, not patented.

*Male, or pollen, parent.*—Proprietary selection of *Spathiphyllum* Schott. identified as code number 20071786-33, not patented.

Propagation:

*Type.*—By tissue culture.

*Time to initiate roots, summer.*—About twelve days at temperatures about 23° C.

*Time to initiate roots, winter.*—About 13 days at temperatures about 23° C.

*Time to produce a rooted young plant, summer.*—About 215 days at temperatures about 21° C.

*Time to produce a rooted young plant, winter.*—About 240 days at temperatures about 21° C.

*Root description.*—Medium in thickness, fibrous; white in color.

*Rooting habit.*—Moderately branching, medium density.

Plant description:

*Plant and growth habit.*—Upright and somewhat outwardly arching plant habit; overall plant shape, broadly inverted triangle; moderately vigorous growth habit.

*Clumping habit.*—Freely clumping habit, bushy and dense growth habit; about eight clumps develop per plant.

*Plant height, from soil level to top of leaf plane.*—About 56.3 cm.

*Plant height, from soil level to top of inflorescences.*—About 77.2 cm.

*Plant diameter or spread.*—About 71.8 cm.

*Leaf description.*—Arrangement: Alternate; simple. Length: About 27.9 cm. Width: About 12 cm. Shape: Narrowly elliptic to narrowly ovate. Apex: Narrowly apiculate. Base: Attenuate. Margin: Entire; slightly undulate. Texture, upper and lower surfaces: Smooth, glabrous; slightly leathery. Luster, upper surface: Glossy. Luster, lower surface: Moderately glossy. Venation pattern: Pinnate. Color: Developing leaves, upper surface: Darker than between N137A and 147A. Developing leaves, lower surface: Close to between 138A and 147B. Fully expanded leaves, upper surface: Darker and more intense than between N137A and 147A; venation, darker than 143A. Fully expanded leaves, lower surface: Close to 137B to 137C; venation, close to 144B. Petiole: Length (including geniculum): About 29.4 cm. Diameter, just below geniculum: About 3.5 mm. Diameter, at plant base: About 8 mm. Texture: Smooth, glabrous. Luster: Slightly glossy. Color, upper and lower surfaces: Darker than 143A. Geniculum length: About 2.7 cm. Geniculum diameter: About 4.5 mm. Geniculum texture: Smooth, glabrous. Geniculum luster: Slightly glossy. Geniculum color, upper and lower surfaces: Close to 143A to 143B. Wing length: About 25.5 cm. Wing diameter: About 9 mm. Wing color: Close to 143C.

Inflorescence description:

*Inflorescence arrangement and flowering habit.*—Slightly cupped erect spathes with columnar spadices held above and between the foliar plane on strong and erect scapes; flowering structures arise from leaf axils; plants begin flowering about five months after planting; freely and continuous flowering year-round under greenhouse conditions in The Netherlands; freely flowering habit, typically about seven inflorescences develop per plant.

*Fragrance.*—Moderately fragrant; fragrance, sweet and pleasant.

*Inflorescence longevity.*—Inflorescences last more than three weeks on the plant; inflorescences persistent.

*Spathe.*—Length: About 21.5 cm. Width: About 7.1 cm. Depth: About 2.9 cm. Shape: Ovate to narrowly ovate. Apex: Apiculate; twisting. Base: Attenuate. Margin: Entire. Texture, upper and lower surfaces: Smooth, glabrous; slightly leathery. Luster, upper and lower surfaces: Slightly glossy. Color: When developing, front surface: Close to 155A; at the apex and main vein, close to 143B. When developing, rear surface: Close to 155B; at the apex and main vein, close to 144A. Fully developed, front surface: Close to NN155B; at the apex, close to 141A; main vein, close to 143C; with development, color becoming closer to N144D and 145B. Fully developed, rear surface: Close to NN155B; at the apex, close to 141B; main vein, close to 143A.

*Spadix.*—Length: About 4.7 cm. Diameter: About 1.3 cm. Shape: Columnar, tapering towards the apex; apex, obtuse; base, obtuse; cross-section, rounded. Aspect: Mostly erect. Color, immature: Between 155A and 160D. Color, mature: Close to 155A and 161D. Flowers: Quantity per spadix: Numerous, about 90. Shape: Rounded. Height: About 3 mm.

Diameter: About 4 mm. Anther color: Close to 155A. Pollen amount: None observed. Stigma shape: Ovoid. Stigma color: Close to 155A. Ovary color: Close to 155A.

*Scape.*—Length: About 62.2 cm. Diameter: About 4.5 mm. Strength: Strong. Aspect: Erect to about 10° from vertical. Color: Close to between 143A and 144A.

*Seeds and fruits.*—Seed and fruit development have not been observed on plants of the new *Spathiphyllum.*

Disease & pest resistance: Plants of the new *Spathiphyllum* have not been observed to be resistant to pathogens or pests common to *Spathiphyllum* plants.

Temperature tolerance: Plants of the new *Spathiphyllum* have been observed to be tolerant to temperatures ranging from about 15° C. to about 36° C.

It is claimed:

1. A new and distinct *Spathiphyllum* plant named 'Spamei' as illustrated and described.

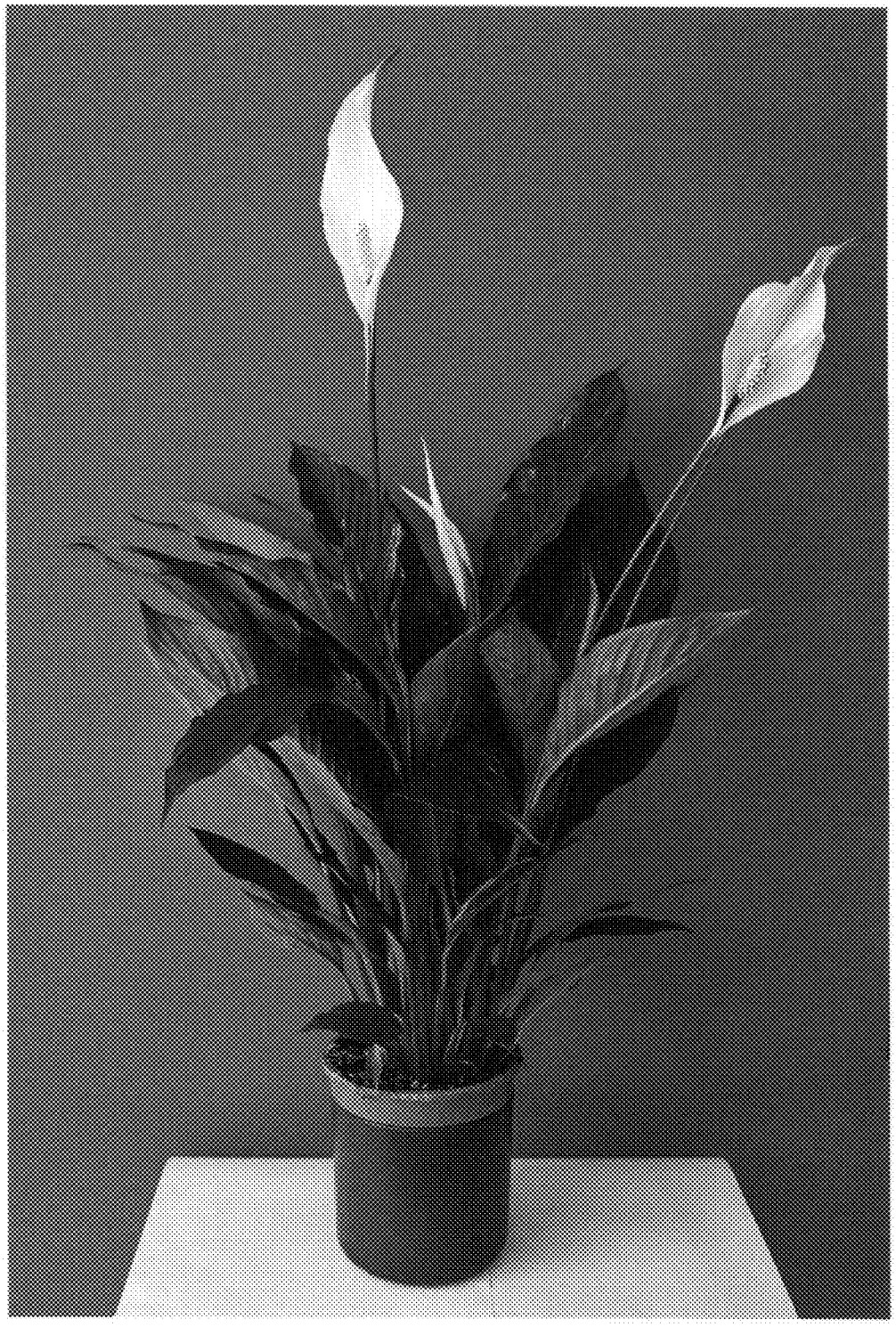

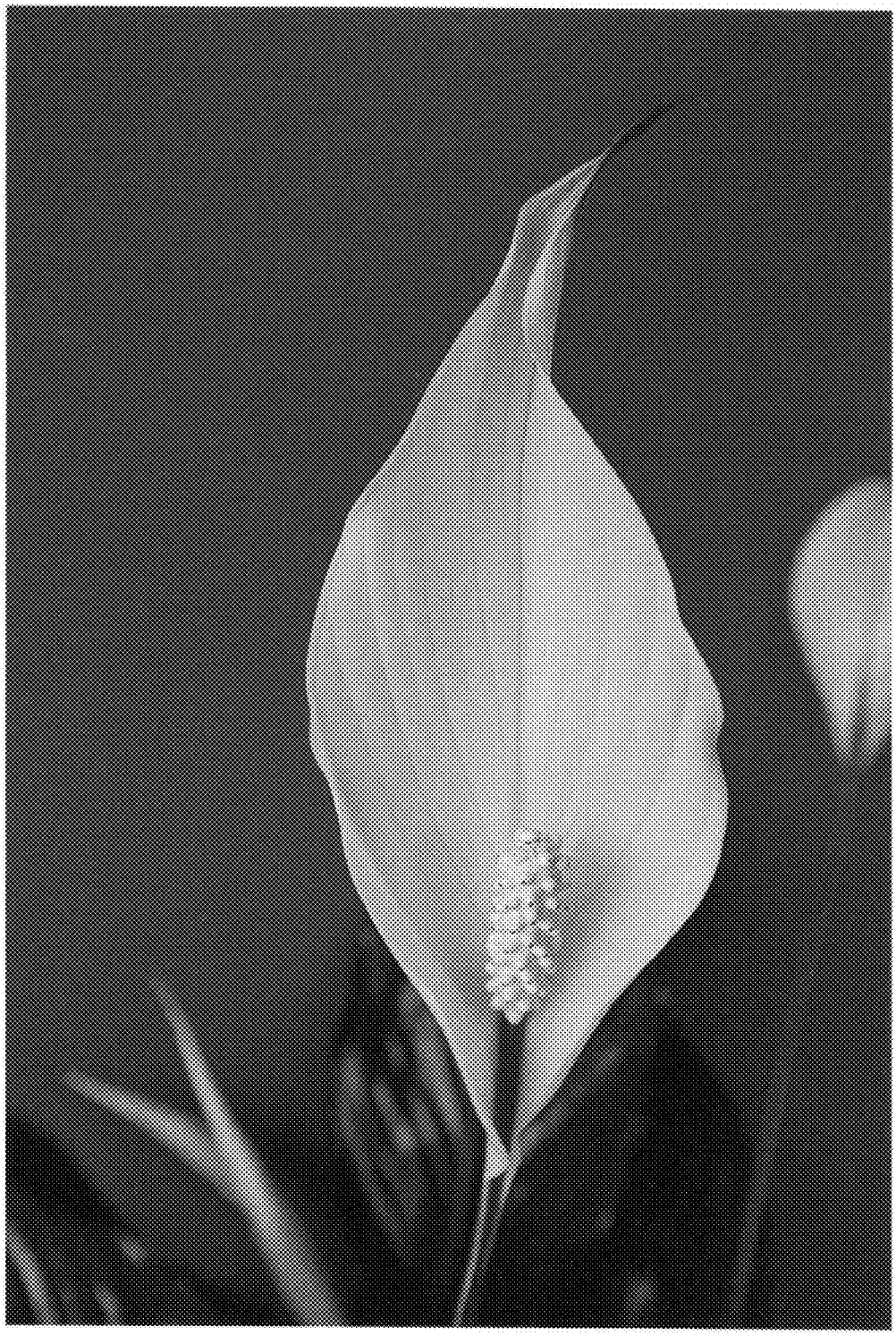

* * * * *